US005896267A

United States Patent [19]
Hittman et al.

[11] Patent Number: 5,896,267
[45] Date of Patent: Apr. 20, 1999

[54] SUBSTRATE MOUNTED FILTER FOR FEEDTHROUGH DEVICES

[75] Inventors: Fred Hittman; Allan S. Gelb; Marcia J. Gelb, all of Baltimore; Thomas N. Foreman; Paul E. Kutniewski, both of Ellicott City, all of Md.

[73] Assignee: Greatbatch-Hittman, Inc., Columbia, Md.

[*] Notice: This patent is subject to a terminal disclaimer.

[21] Appl. No.: 08/891,092

[22] Filed: Jul. 10, 1997

[51] Int. Cl.$^6$ ................................. H01G 4/35
[52] U.S. Cl. .................. 361/302; 361/303; 29/25.42
[58] Field of Search ................... 361/302, 303; 174/143, 152 R, 152 GM; 333/182–184; 29/854–855, 25.42

[56] References Cited

U.S. PATENT DOCUMENTS

| | | | |
|---|---|---|---|
| 4,144,509 | 3/1979 | Boutros | 333/181 |
| 4,148,003 | 4/1979 | Colburn et al. | 333/181 |
| 5,032,692 | 7/1991 | DeVolder | 174/52.3 |
| 5,546,058 | 8/1996 | Azuma et al. | 333/183 |
| 5,650,759 | 7/1997 | Hittman et al. | 333/182 |

Primary Examiner—Kristine Kincaid
Assistant Examiner—Anthony Dinkins
Attorney, Agent, or Firm—Rosenberg, Klein & Bilker

[57] ABSTRACT

Filtered feedthrough assembly (100, 200) is formed by mounting a filter support assembly (130, 130', 230) having a capacitor (110,210) mounted thereto, to a conductive feedthrough (10, 10'). The conductive feedthrough includes a metallic ferrule (14, 14') having a centrally disposed through opening (28) extending between opposing ends thereof. At least one elongate lead wire (12) extends through the ferrule through opening. A hermetic seal insulator (20, 20') is disposed within the central opening of the ferrule and is sealed thereto. The filter support assembly (130, 130', 230) includes an insulative substrate (132, 132', 132") having a first metallization pattern (133, 314) formed on an upper surface (138, 138") thereof. A second metallization pattern (135, 316) is formed on the lower surface (124, 124') of substrate (132, 132', 132"). A capacitive element (110, 210) is electrically coupled between a first metallization area (145, 318) and second metallization area (143,320) of the first metallization pattern (133, 314). The first metallization area (145, 318) is electrically coupled to the lead (12) and the second metallization area (143, 320) is electrically coupled to the ferrule (14, 14'). The second metallization area (145, 318) includes a metallized recess (140, 140') formed in a perimeter edge (134, 134') of the substrate (132, 132', 132"). A conductive contact material (150) is disposed within the recess for providing the electrical connection to the ferrule (14, 14'). A conductive contact material (152) provides the electrical connection between the lead (12) and the first metallization area (145, 318).

30 Claims, 6 Drawing Sheets

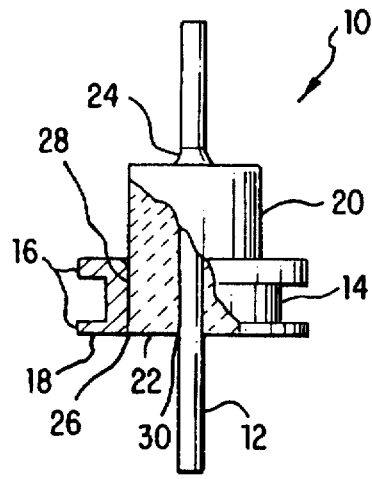
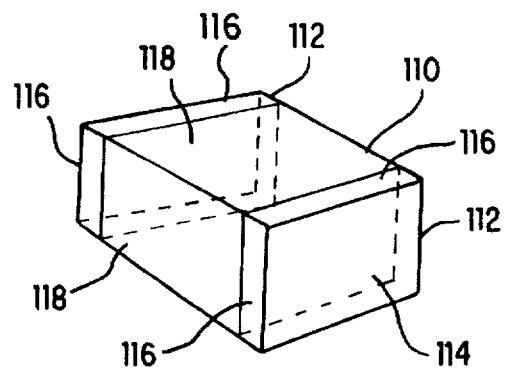
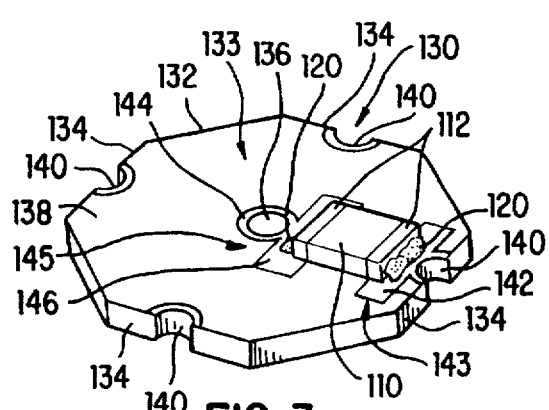
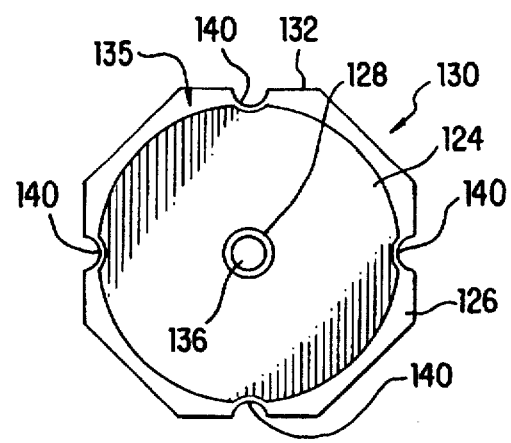
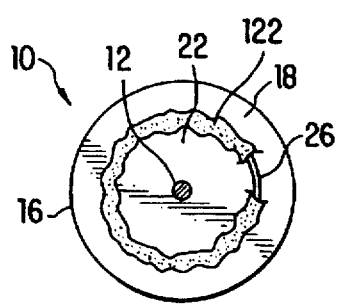
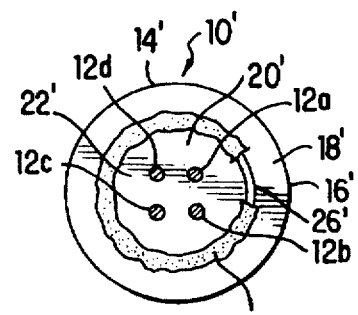

SUBSTRATE MOUNTED FILTER FOR FEEDTHROUGH DEVICES

BACKGROUND OF THE INVENTION

1. Field of the Invention

This invention is directed to a filtered feedthrough assembly having at least one lead wire. In particular, this invention directs itself to a feedthrough assembly utilizing at least one capacitor element coupled between the lead wire and a metallic ferrule of the feedthrough. Still further, this invention directs itself to a filtered feedthrough for use in implantable medical devices wherein the capacitor is affixed to an insulative substrate, with the substrate being secured to the conductive feedthrough device. Still further, this invention directs itself to a filtered feedthrough wherein the substrate has a polygonal contour with at least a portion of the edges thereof having metallized recesses formed therein. The metallized recesses define spaces into which conductive contact material may be applied to provide an electrical connection with the metallic ferrule of the feedthrough device.

2. Prior Art

Filtered feedthrough devices are well known in the art. The best prior art known to the Applicants include U.S. Pat. Nos. 3,329,911; 3,443,251; 3,617,830; 3,879,691; 4,152,540; 4,314,213; 4,424,551; 4,642,589; 4,673,900; 4,675,629; 4,682,129; 4,698,605; 4,700,155; 4,700,440; 4,772,225; 4,791,391; 4,804,332; 4,819,130; 4,853,824; 4,872,085; 4,887,185; 4,984,129; 5,032,949; 5,150,086; 5,153,540; 5,206,786; 5,132,522; 5,287,076; 5,333,095; 5,406,444; and the following Publications: "Cellular Phones May Affect Use of Pacemakers", *The Wall Street Journal*, Friday, Apr. 28, 1995, pp. B1–B3; "EMI Filtering in Medical Implantables", *Medical Devices in Diagnostic Industry*, September 1994; "Do European GSM Mobile Cellular Phones Pose a Potential Risk to Pacemaker Patients?", *Pace*, Vol. 18, June 1995, pp. 1218–1224; and, "Ceramic EMI Filters—A Review", *Ceramic Bulletin*, Vol. 67, No. 4, 1988, pp. 737–746.

Filtered feedthrough devices have been employed in implantable devices, as disclosed in U.S. Pat. No. 4,152,540 and the publication entitled "EMI Filtering in Medical Implantables". Such filtered feedthrough devices are known to employ discoidal capacitors in single lead feedthrough devices and discoidal capacitor arrays in multi-lead assemblies. Many of such feedthrough devices incorporating such capacitive elements had to be specially manufactured to provide a cavity into which the capacitor or capacitor array was to be located, either by creating a recess within the ceramic hermetic sealing element, or extending the metallic ferrule beyond the hermetic seal in order to form such a cavity.

Whereas in the instant invention, individual capacitive elements are positioned on a separate substrate which is subsequently married to the feedthrough. By this arrangement, filtering can be added to a conventional feedthrough device without the requirement for manufacturing special parts, thereby improving the efficiency of the manufacturing operation. Further, the substrate mounted capacitor assembly can be tested prior to its marriage with the conductive feedthrough.

In still other prior art devices, such as disclosed in U.S. Pat. No. 3,617,830, filtered feedthrough devices utilizing chip capacitors are disclosed. Such prior art devices disclosed chip-type filter capacitors positioned between a pair of conductive rings, with the space between the capacitors and the rings being encapsulated with an epoxy filler material. In addition to such materials not providing a high reliability hermetic seal, nor providing a biocompatible structure, such structures do not provide for accommodating capacitors of different sizes, as the chip capacitor is located within a cavity defined by the space between the conductive rings. Therefore, a different diameter outer ring is required for an application requiring larger capacitors, and in any one application all of the capacitors must be the same length irrespective of their capacitive value. With the chip capacitors being disposed within a cavity, the difficulty in replacing any one capacitor, which proves to be defective, is almost as difficult as in the case where discoidal capacitors are utilized.

In systems such as that disclosed in U.S. Pat. No. 4,152,540, and other prior art systems such as that disclosed in U.S. Pat. Nos. 4,424,551 and 5,333,095, filtered feedthrough devices employing discoidal type capacitors are electrically coupled to the respective lead wires and ferrules utilizing conductive adhesive compositions. The system disclosed by U.S. Pat. No. 5,333,095 provides no means for applying a moisture resistant coating to the discoidal capacitive element which has a diameter substantially larger than that of the feedthrough device, making such impractical for use in most modern implantable systems wherein space is at a premium and where the feedthrough devices are manufactured by other than the implantable device manufacturer.

It has long been known that medical implantable devices must operate in an environment which is subjected to electromagnetic interference (EMI). The electrical leads which extend from such implantable devices act as antennas which receive and conduct electromagnetic energy into the electronics of the implanted device. Since the circuits of such medical implantable devices are very sensitive, and reliability is so important, as a fault may be life threatening, medical implantable devices have incorporated filter circuits therein to suppress EMI. In some cases, feedthrough devices employing discoidal type capacitors have been employed in an attempt to filter out the electromagnetic interfering signals before they reach the electronic circuitry of the implantable device. The ability to filter the interference before it reaches the electronics has become more important recently, with the discovery that the electromagnetic interference generated by the new digital cellular phones and other electronic devices is not sufficiently suppressed by prior art electromagnetic interference filters of some current medical implantable devices. The high frequency emissions from the digital cellular phones may be re-radiating within the medical implantable device, bypassing and thereby rendering the "on-board" filters ineffective. It is therefore critical that the filtering take place as close to the source of the emissions as possible, such as at the entrance to the housing of the implantable device. As a result of this ever increasing problem, the use of filtered feedthroughs is increasing and may soon be required by governmental agencies to effectively suppress EMI, and therefore it will be important to efficiently manufacture such, in order to help contain the costs of the implantable medical devices.

Further, for medical devices such as implantable defibrillators, the high voltage output through the feedthrough devices adds another complexity to incorporating a filter capacitor therewith. A capacitor employed in such a device must be physically larger in order to withstand the higher voltage which must be impressed thereon, but the space limitations of the feedthrough used in such defibrillators are not conducive to accommodating large size capacitors. However, utilizing the filtered feedthrough of the present invention, such larger capacitors can be installed without requiring an increase in the physical size of the feedthrough structure. Still further, to suppress high frequency EMI, each lead of a multi-lead feedthrough assembly may be required to be individually tuned, thus, each lead may require a capacitor having a different capacitance, voltage rating or the like, which can be installed in the present invention.

SUMMARY OF THE INVENTION

A filtered feedthrough assembly is provided. The filtered feedthrough assembly includes a conductive feedthrough including (a) a metallic ferrule having opposing first and second ends and a centrally disposed through opening extending between the first and second ends, (b) at least one elongate lead wire extending through the ferrule through opening, and (c) a hermetic seal between the lead wire and the ferrule disposed within the ferrule through opening. The filtered feedthrough assembly also includes a filter support assembly disposed at an end surface of the conductive feedthrough. The filter support assembly includes an insulative substrate having at least one aperture formed therein for passage of the lead wire therethrough. The substrate has an upper surface with at least one first metallization area formed adjacent to the at least one aperture and at least one second metallization area disposed adjacent a perimeter portion thereof. The filtered feedthrough assembly further includes at least one capacitor disposed on the filter support assembly coupled between the first metallization area and the second metallization area. The first metallization area is electrically coupled to the lead wire and the second metallization area is electrically coupled to the ferrule.

BRIEF DESCRIPTION OF THE DRAWINGS

FIG. 1 is an elevation view, partially cut away, of a conventional feedthrough device;

FIG. 2 is a perspective view of a chip capacitor utilized in the present invention;

FIG. 3 is a perspective view of a filter support assembly of the present invention;

FIG. 4 is a plan view of a lower surface of the filter support assembly of the present invention;

FIG. 5A is a plan view, partially cut away, of a feedthrough with a bead of adhesive applied thereto;

FIG. 5B is a plan view, partially cut away, of a multi-lead feedthrough with a bead of adhesive applied thereto;

DESCRIPTION OF THE PREFERRED EMBODIMENTS

Figure 5C:
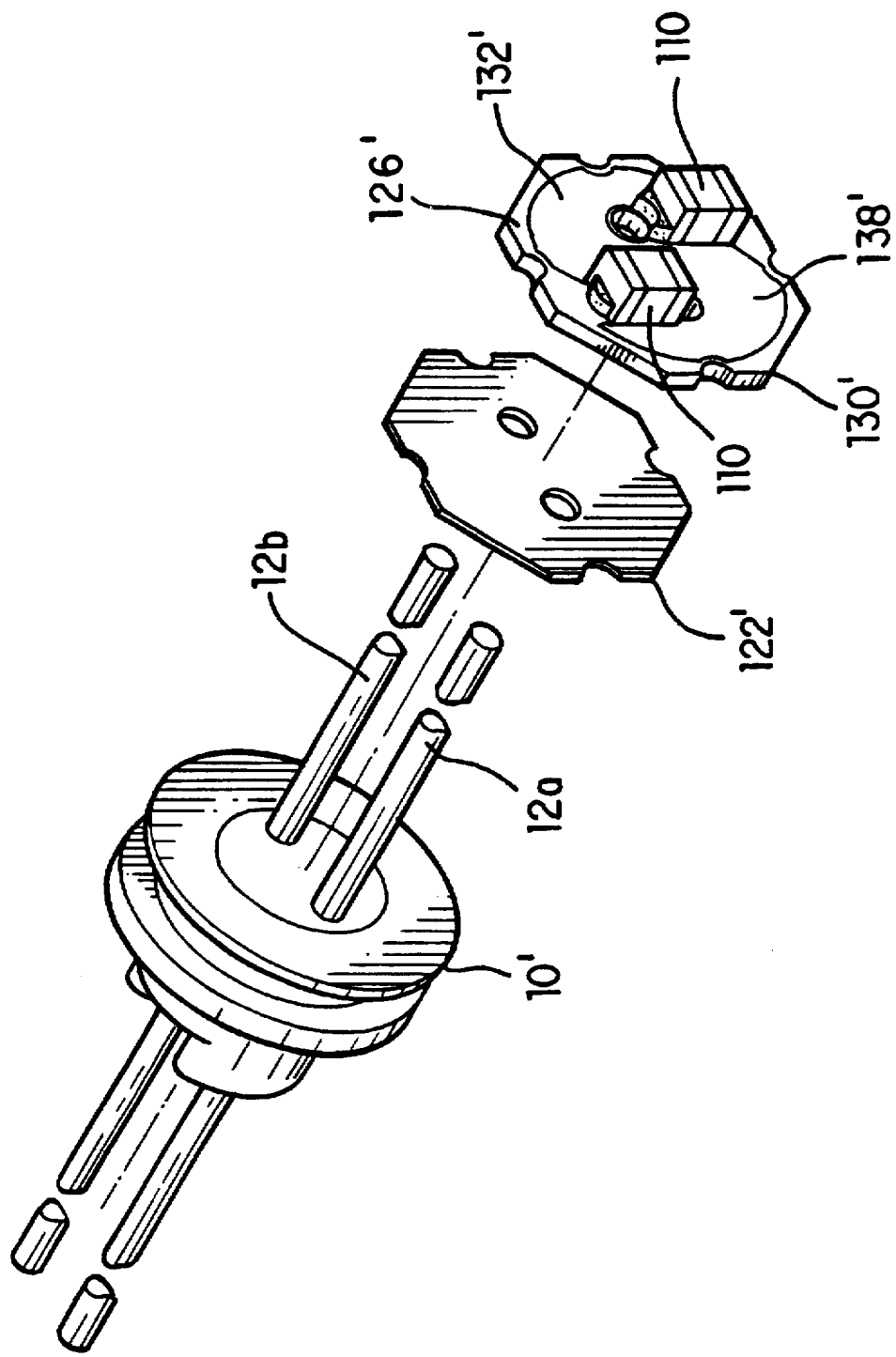
FIG. 5C is a perspective exploded view of a multilead feedthrough showing use of an insulating sheet between the feedthrough and the filter support assembly.
Figure 6:
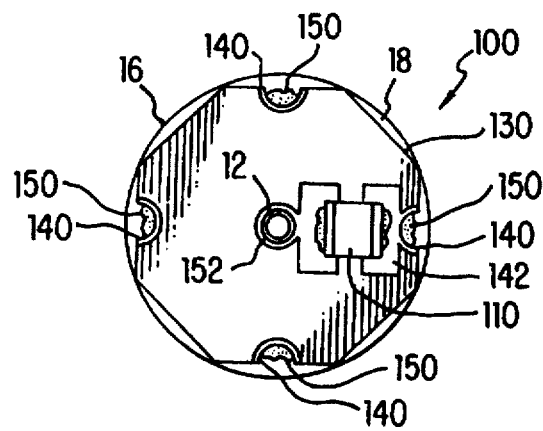
FIG. 6 is a plan view showing the capacitor support assembly assembled to the conductive feedthrough device.

Referring to FIGS. 3 through 13, there is shown, filtered feedthrough assemblies 100, 200 for use in implantable medical devices. Implantable devices utilized in the medical and biological sciences that require signals to be input thereto, or provide output signals, or provide output signals, are susceptible to interference from various sources of the electromagnetic radiation. In addition to such implantable devices requiring protection from spurious electromagnetic radiation, such devices must be protected from infiltration of bodily fluids and migration of toxic materials therefrom.

The most common implantable devices in use today are pacemakers and defibrillators. Both of these devices require one or more electrodes to be coupled from the device to the implant recipient's heart muscle. Electronics for such devices are typically housed in a titanium case which is hermetically sealed, as by laser welding. The electrical connection between the electronics within the housing and the external electrodes is made through a device known as a feedthrough, such as the conductive feedthrough 10, shown in FIG. 1.

The conventional feedthrough 10 is shown as being a single lead feedthrough, however, such devices are readily available in multiple lead assemblies, which may have any number of leads, and are commonly produced with two, three, four, five or six leads. Feedthrough 10 includes a metallic ferrule 14 having a central through opening 28 formed therein. Ferrule 14 may have one or more flanges 16 formed therein to facilitate mounting to the implantable medical device, and may be circular, oblong, or rectangular in cross-sectional contour. Ferrule 14 may be formed of material such as titanium, niobium, tantalum, or alloys thereof. A lead wire 12 extends through the opening 28 and is sealed with an insulator 20, the insulator 20 having a central through bore 30 for passage of lead wire 12 and an outside diameter dimensioned to fill the remainder of opening 28. Lead wire 12 may be formed of materials such as platinum, platinum/iridium, niobium, titanium, tantalum, or combinations thereof. The insulator 20 may be a high temperature glass composition wherein metal-to-glass seals are formed at the perimeter of the openings 28 and 30. Insulator 20 may alternately be formed of a ceramic material composition, in which case the insulator is bonded to the lead wire 12 and ferrule 14 by the brazed joints 24 and 26, respectively. The brazed joints 24 and 26 may be accomplished with such materials as gold, a gold alloy or a titanium alloy.

Feedthrough 10 is provided with an insulator 20 having an end surface 22 that may be disposed in coplanar relationship with the end surface 18 of ferrule 14, the end surfaces 18 and 22 being disposed within the housing of the implantable medical device, allowing conduction of signals on the lead wire 12 while maintaining a hermetic seal. Alternately, the sides of the ferrule can be extended to form a well into which filter capacitors may be disposed.

Referring now to FIG. 2, there is shown, a "chip capacitor" 110, a commercially available device having a parallelepiped ceramic body with a pair of metallized contacts 112 formed on opposing ends thereof. Each metallized contact 112 includes a conductive end portion 114 and a plurality of conductive segments 116 disposed on each side 118 of chip capacitor 110, at the endmost regions thereof. By such arrangement, electrical coupling can be made with side portions of the chip capacitor, as well as end portions thereof.

Figure 7:
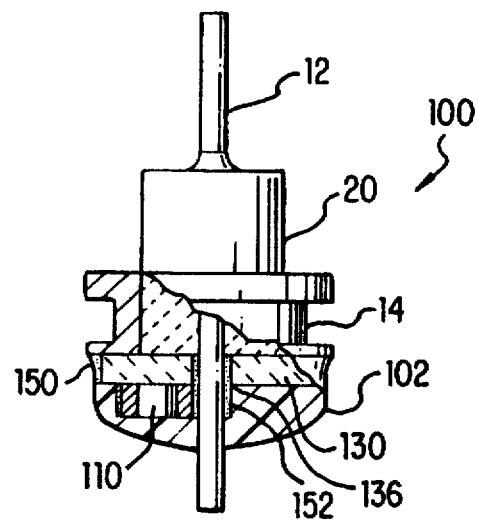
FIG. 7 is an elevation view, partially cut away, of a single lead embodiment of the present invention.

A filtered feedthrough 100, as shown in FIG. 7, is constructed utilizing a chip capacitor 110 which is added to a capacitor support assembly 130 and the assembly added to the feedthrough 10. Although only one capacitor 110 is shown, it should be understood that multiple capacitors may be coupled to the lead wire 12 by providing the appropriate metallization areas therefor on the surface of the substrate 132. In such a configuration, the capacitors could be coupled in parallel relationship to increase the effective capacitance or take advantage of differing high frequency characteristics the capacitor might have. Chip capacitor 110 is electrically coupled to the lead wire 12 on one end, and electrically coupled to the ferrule 14 on the opposing end, by means of the metallizations formed on the substrate 132. While capacitor 110 is shown as being mounted on the capacitor support assembly 130, in other configurations the capacitor may be located elsewhere on the feedthrough device, such as on a side portion thereof, with substrate extended such that the metallization on the substrate 132 provides an electrical connection between one of the contacts 112 of capacitor 110 and the lead 12 of the feedthrough.

As shown in FIGS. 3 and 4, a capacitor support assembly 130 is formed by an insulative substrate 132 having an upper surface 138 with a first metallization pattern 133 formed thereon. The opposing surface 124 of substrate 132 has a second metallization pattern 135, and a metallized aperture 136 extends between upper surface 138 and lower surface 124 formed thereon. The designation of surfaces 138 and 124 as supper and lower is arbitrary, either surface could be positioned to overlay the end surface 22 of the feedthrough insulator 20. The capacitor 110 is disposed with each of its contacts 112 being positioned contiguous first and second metallization areas 145 and 143. When assembled to the feedthrough 10, the lead wire 12 will extend through the aperture 136 and be electrically connected to a metallized annular region 144 of the first metallization area 145, and the metallized annular wall of the aperture 136. Only one annular region 144, 128 is required for coupling to the feedthrough leads, the use of both is optional. Substrate 132 is formed of an insulation material having a generally polygonal contour with a plurality of angularly spaced metallized edge recesses 140 formed therein. Substrate 132 may be formed of glass, ceramic or polymer compositions and be shaped in a contour adapted to mate with a particular feedthrough structure being used. In one working embodiment, substrate 132 is formed of an alumina composition. The recesses 140 are each formed in a respective perimeter edge 134 and have an arcuate wall that is metallized. Each recess 140 may therefore form a substantially semicircular indentation in each respective edge portion 134. Adjacent a respective metallized recess, and electrically coupled thereto, the second metallization area 143 includes a metallized upper edge region 142 to which the capacitor 110 is electrically coupled. In addition to annular region 144, the first metallization area 145 includes a metallized extended area 146 electrically coupled to the annular region 144, to provide an electrical contact area for coupling to capacitor 110. Where multiple capacitors are to be coupled to the lead 12, multiple metallized upper edge regions are provided adjacent other of the metallized edge recesses 140 and additional metallized extended areas 146 are provided in correspondence therewith.

The bottom surface 124 of the substrate 132 is provided with a second metallization pattern 135. Metallization pattern 135 includes a metallized annular region 128 which circumscribes the metallized through opening 136 and is electrically coupled thereto. Further, the second metallization pattern 135 may include a perimeter edge metallization 126, the perimeter edge metallization 126 defining a substantially annular area disposed adjacent the polygonal perimeter edge and electrically coupled to each of the plurality of metallized recesses 140. Perimeter edge metallization 126 may be disposed on the opposing side of the substrate 132. While the capacitor 110 may be coupled to the substrate 130 subsequent to the securement of the substrate to the feedthrough, assembling the capacitor to substrate prior to the assembly of the substrate to the feedthrough provides manufacturing advantages. Where a subassembly is formed by coupling the capacitor to the first metallization pattern on the substrate 132, prior to the substrate being secured to the feedthrough, such may be pretested and burned in prior to the subassembly being married to the feedthrough device. Such improves the efficiency of the manufacturing operation in that when defects are found, they are more easily corrected, or where not correctable, may be discarded. The discarding of the capacitor/substrate subassembly is far more economical than would otherwise be the case if such had been joined to the feedthrough and the whole assembly discarded.

In joining the capacitor to the substrate, each of the contacts 112 of capacitor 110 must be electrically coupled to a respective one of the metallized areas 142 and 146. The capacitor 110 may be first secured on substrate 132 and then electrically coupled to the respective metallized areas by an electrically conductive material 120. Alternately, the conductive material 120 may serve the dual role of securing the capacitor to the substrate and providing the electrical coupling therebetween. The electrically conductive material 120 may be a solder or braze material, or alternately a conductive glass, conductive epoxy or conductive polyimide composition. A commercially available conductive polyimide composition having a Trade Name "ABLEBOND 71-1" has been successfully utilized for providing electrical coupling of capacitor 110 to metallized regions 142, 146.

In one operable method for forming a capacitor/substrate subassembly, a quantity of conductive polyimide adhesive is first applied to the two metallized areas, or pads 142, 146, and then the capacitor 110 is seated on the substrate with the respective conductive segments 116 of the metallized contacts 112 juxtaposed thereon. The conductive adhesive is cured in a two-step process. In the first step, the capacitor/substrate subassembly is maintained at 150° C. for approximately 30 minutes. Between this first step and the next step of the cure process, the subassembly may be electrically tested and repaired as necessary. In the second step of the curing process, the capacitor/substrate subassembly is maintained at 275° C. for approximately thirty minutes. Subsequent to cooling, the capacitor/substrate subassembly may be retested, burned in, and/or mated with the feedthrough 10.

A non-conductive adhesive or solid sheet of insulating material is utilized between the substrate 132 and the feedthrough 10, to prevent any short circuits from developing between the lead 12 and ferrule 14, and to aid in securing the substrate to the feedthrough. As shown in FIG. 5A, an annular bead of non-conductive adhesive or bonding material 122 is formed around the perimeter edge of the insulator top surface 22, overlaying the seal 26 and in concentric relationship with the lead 12. Alternately, a continuous layer of non-conductive material may be used. That material may be a material which is subsequently cured or a material which is a preformed sheet material. The capacitor support assembly 130 is then positioned such that the lead 12 extends through the metallized aperture 136 and the annular bead of non-conductive epoxy 122 contacts the bottom surface 124 of substrate 132. The bead or layer of adhesive 122 forms a dam on the lower surface 124 of substrate 132, between the metallized annular region 128 and the perimeter edge metallization 126, thereby preventing any flow of conductive adhesive therebetween during subsequent processing steps. The non-conductive material may be formed by a glass composition, a polyimide, acrylic, epoxy or other polymer, in solid film liquid or gel form. In one embodiment, a commercially available polyimide composition having the Trade Name "ABLEBOND 71-2" has been utilized to form the non-conductive insulating material 122. In another embodiment, a sheet of polymer film 122' has been utilized to prevent the flow of the conductive contact material beneath the substrate 132, as shown in FIG. 5C.

The non-conductive insulative material 122 may be at least partially cured before applying a conductive material to electrically join the first metallization area 145 to the lead 12 and the metallized edge recesses 140 to the ferrule 14. Thus, the polyimide adhesive 122 may be subjected to heating at 150° C. for approximately thirty minutes. Electrical coupling to the lead 12 and ferrule 14 is accomplished with a conductive material which may be in the form of a conductive glass, conductive polymer, or a metallic composition to provide a soldered or brazed connection. Such conductive material forms the conductive contact material 150 which is applied within each of the recesses 140 formed in a plurality of the side edges 134. That conductive material also forms the conductive contact material 152 which is applied within the metallized aperture 136 around the lead 12 to provide electrical contact therebetween. In one working embodiment, the conductive contact material 150, 152 is a conductive polyimide composition having the Trade Name "ABLEBOND 71-1". The polyimide conductive contact materials are then subjected to a first cure step, wherein the device is maintained at 150° C. for approximately thirty minutes. Subsequently, the assembly is subjected to a second cure step wherein such is maintained at a temperature of 275° C. for approximately thirty minutes. After fully curing the polyimide compositions and subsequently allowing such to cool, the end of the device carrying the capacitor 110 is potted, encapsulating the capacitor in a moisture resistant composition 102, which may be formed by an epoxy, polyimide, silicon or other polymer composition. The device is then heated to a predetermined temperature for a specified time period in order to cure the encapsulant. In one working embodiment, a polyimide composition having the Trade Name "ABLEBOND 933-1" was successful utilized as the encapsulant 102, and cured at a temperature of 125° C. for a time period approximating two hours.

Figure 10:
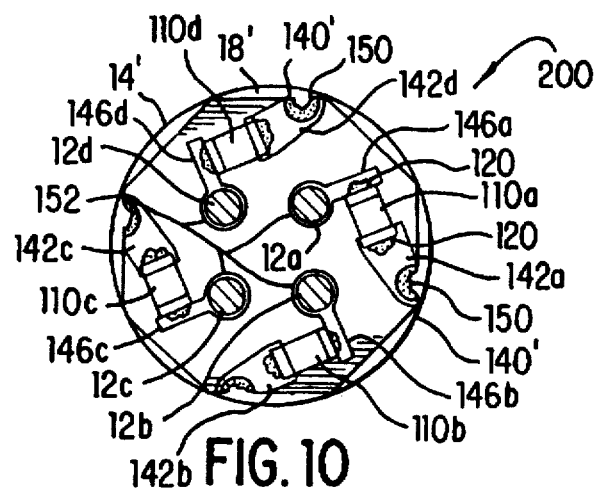
FIG. 10 is a top plan view showing the multi-lead capacitor support assembly of the present invention assembled to a multi-lead feedthrough device.

Referring now to FIG. 10, there is shown, a multi-lead filtered feedthrough 200 which incorporates a capacitor support assembly 130'. The feedthrough with which the capacitor support assembly 130' is combined is structured like that of the single lead feedthrough shown in FIG. 1, but with the hermetic seal insulator 20 having multiple through bores 30 formed therein for receiving multiple leads 12a–12n. In the example of FIG. 10, a four lead feedthrough is shown, wherein each lead 12a–12d is electrically coupled to a respective filter capacitor 110a–110d. Each of the capacitors 110a–110d may be of a different capacitance value, voltage rating or other characteristic, and may be of different physical size as well. As in the single lead embodiment, capacitor support assembly 130' includes a substrate 132' formed of an insulative material and having an upper surface 138' with a first metallization pattern 314 formed thereon. First metallization pattern 314 includes a first metallization area 318 and a second metallization area 320.

Figure 8:
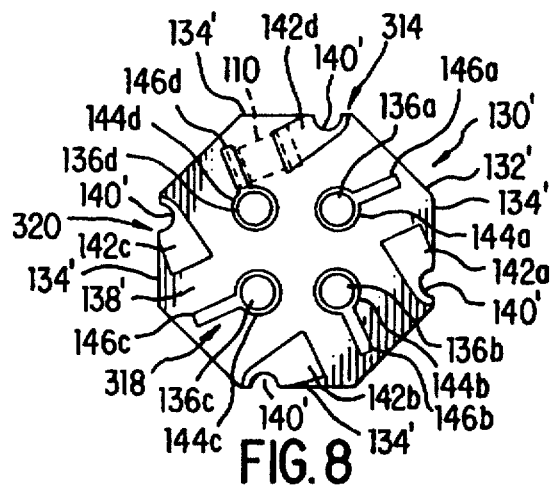
FIG. 8 is a top plan view of the capacitor support assembly of the present invention with the location of a capacitor shown in phantom.
Figure 9:
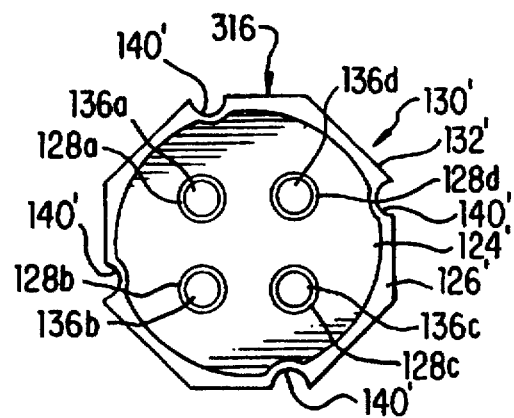
FIG. 9 is a plan view of the capacitor support assembly of the present invention showing the lower surface thereof.

As shown in FIGS. 8 and 9, substrate 132' is provided with a plurality of metallized apertures 136a, 136b, 136c and 136d, the number corresponding to the number of lead wires 12 of the particular feedthrough to which the assembly 130' is to be added. The first metallization area 318 is associated with the metallization disposed adjacent to the apertures 136a–136d. The second metallization area 320 is disposed adjacent metallized edge recesses 140' disposed in particular edge portions 134' of the polygonal perimeter edge of substrate 132'. First metallization area 318 includes metallized annular regions 144a, 144b, 144c and 144d, each metallized annular region circumscribing a respective one of the metallized through bores 136a–136d, and the metallized walls of the through bores 136a–136d. First metallization area 318 also includes metallized extended areas 146a, 146b, 146c and 146d, which metallized regions extend from a respective metallized annular region 144a–144d at a predetermined angle. The second metallization area 320 includes metallized upper edge regions 142a, 142b, 142c and 142d, which regions are electrically coupled to a respective metallized edge recess 140'. The metallized regions 142a–142d and 146a–146d provide the connection pads to which respective capacitors 110 are coupled.

Where multiple capacitors are being incorporated in a feedthrough device, it is particularly advantageous to have the ability to pretest a subassembly before final installation, so as not to have to scrap and thereby waste an entire device due to the failure of the single component. Therefore, where such a subassembly is being utilized, the capacitors 110 are affixed to the substrate 130' by the conductive material 120, either alone or in combination with a non-conductive adhesive applied to a region of the upper surface 138' of substrate 132' between respective metallization regions 146a–146d and 142a–142d. Subsequently, the assembly is heated to provide a partial cure of the adhesive materials, as has been previously described. The capacitor support assembly 130' may then be electrically tested to insure that each capacitor is performing up to the required specification. Subsequent to passing all testing, and after replacement of any defective capacitors, the assembly 130 may then be further exposed to a predetermined temperature to complete the curing process. Subsequently, the capacitor support assembly 130' is joined to the multi-lead feedthrough device, as shown in FIG. 10, with the substrate being juxtaposed over the end surface of the insulator and ferrule.

Turning now to FIG. 5B, there is shown, a top view of the multi-lead feedthrough 10' having a ferrule 14' with at least one flange 16', the ferrule having an end surface 18'. Within a central through opening of the ferrule 14' there is disposed a hermetic seal insulator 20' with a top surface 22'. Extending through respective openings formed in the hermetic seal insulator are respective leads 12a, 12b, 12c and 12d. The interface between ferrule 14' and hermetic seal insulator 20' is a seal 26', like that of the single lead feedthrough, previously discussed. As in the single lead embodiment, an annular bead of non-conductive adhesive 122 may be added to circumscribe the four leads 12a–12d. The bead 122 is disposed essentially over the seal 26' to provide a dam for preventing the flow of conductive material applied to either of the leads 12a–12d or the ferrule end surface 18' from flowing to the other. The annular adhesive bead 122 additionally aids in the bonding of the capacitor support assembly 130' to the feedthrough 10'.

Alternately, the non-conductive material can be applied as a continuous coating on the end of the feedthrough to form a dam against the flow of conductive material applied to the leads 12a–12d and aid in bonding the capacitor support to the feedthrough. Another method for preventing a flow of conductive material between the substrate 132' and the feedthrough 10' is by use of a sheet of insulating film 122'. As shown in FIG. 5C, the insulating film 122' is shaped in a contour to match that of the substrate 132'. Insulating film 122' is disposed between the multilead feedthrough 10' and the capacitor support assembly 130'. While a two lead feedthrough is depicted, the disclosed arrangement is applicable to feedthrough assemblies of any number of leads.

Conductive material 150 is applied within each of the metallized edge recesses 140' to provide an electrical connection between the respective metallized upper edge region 142a–142d with the ferrule 14. The conductive material 150 further aids in bonding the capacitor support assembly 130' to the feedthrough 10' and may be the only bonding material if the insulative material 122 is omitted. As is the case for the single lead feedthrough, conductive material 152 is applied within the apertures 136a–136d around each of the respective leads 12a–12d, providing an electrical connection to the metallized annular region 144a–144d, and thereby providing an electrical coupling to a respective end of each capacitor 110 through the metallized extended areas 146a–146d. After appropriate curing, an encapsulant may be applied to overlay the assembly 130' and the capacitors carried thereby, followed by an appropriate curing operation for the encapsulant. Thus, the filtered feedthrough 200 is simply a multi-lead version of the filtered feedthrough 100 shown in FIG. 7.

The substrate 132' of the capacitor support assembly 130' includes a bottom surface 124' having a second metallization pattern 316 formed thereon. Second metallization pattern 316 includes metallized annular regions 128a, 128b, 128c and 128d disposed around each of the respective metallized apertures 136a–136d and electrically coupled to the respective metallized walls of those apertures. The second metallization pattern 316 may further include a perimeter edge metallization 126' which electrically couples each of the metallized edge recesses 140', one to another. The perimeter edge metallization 126' may alternatively be formed on the upper surface 138 of substrate 132'. The designation of upper and lower to the surfaces of the substrate is arbitrary, as either surface may be positioned adjacent the end surface of the feedthrough. Further, the use of annular regions 144a–144d and annular regions 128a–128d is optional, as only one side of the substrate need be adapted for electrical coupling to the feedthrough's leads. Thus, when the conductive contact material 150 is applied to each of the recesses 140', such provides parallel conductive paths between the ferrule 14' and one contact of each of the capacitors 110a–110d. By that arrangement, redundant paths are provided such that if one of the electrical joints formed by the conductive contact material 150 were to open, such would not provide an uncoupling of any of the capacitors. Thus, it would take a failure of each and every one of the connections formed by the conductive contact material 150 to result in a failure of the filter circuit. The avoidance of a failure of the filter circuits is critically important for medical implantable devices, which objective is achieved by the inclusion of the perimeter edge metallization 126, 126'.

Depending on the application and the frequencies from which the circuit is to be protected, the physical dimensions of the capacitors 110a–110d can vary greatly in size. Thus, it is important that the first metallization pattern 314 be laid out so as to accommodate capacitors which would be larger in dimension than the distance between the lead 12 and an adjacent perimeter edge of the substrate 130, 130'. To solve this problem, the metallized extended areas 146a–146d are offset so that the capacitor is angled with respect to an adjacent perimeter edge 134' of the substrate 130'.

Figure 13:
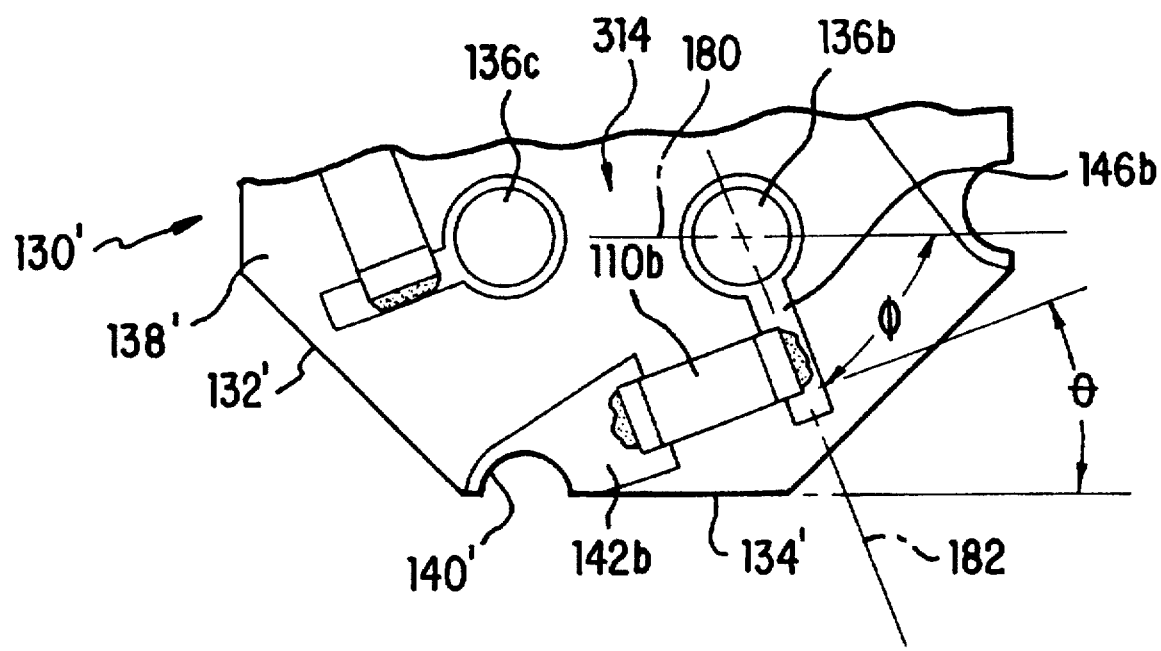

Referring now to FIG. 13, there is shown an enlarged cut-away view of the substrate 132'. Although a multi-capacitor arrangement is being illustrated, it should be understood that the first metallization pattern 133 of the substrate 132 may be similarly laid out. With reference to a center line 180 which extends through the centers of the apertures 136c and 136b, the metallized extended area 146 extends at an angle $\phi$ therefrom, as represented by the center line 182. The capacitor 110b which extends between the metallized extended area 146b and the metallized upper edge region 142b extends perpendicular to the center line 182, thereby extending at an angle $\theta$ with respect to the perimeter edge portion 134'. Depending on the size of the capacitors to be accommodated, the angle $\phi$ may fall within the approximating range of 45°–90° and the angle $\theta$ will correspondingly fall within the range of 45°–0° with respect to the adjacent perimeter edge 134'. Most capacitors will be accommodated where the angle $\phi$ is within the range of 60°–75° and the angle $\theta$ is within the range of 30°–15°, accordingly. In one working embodiment, the metallized extended areas 146 were disposed at an angle $\phi$ equaling 69°, thereby orienting the respective capacitors at an angle $\theta$ equaling 21°. As previously mentioned, in some applications it may be necessary to locate the capacitors in some place other than on the substrate 132'. In such cases, the first metallization pattern 314 will provide a connection between the respective leads 12a–12d and one connection terminal of a respective capacitor 110a–110d. Under such condition, the first metallization pattern may be formed on the surface of the substrate which when applied to the feedthrough faces the insulator cap surface 22'.

Figure 12:
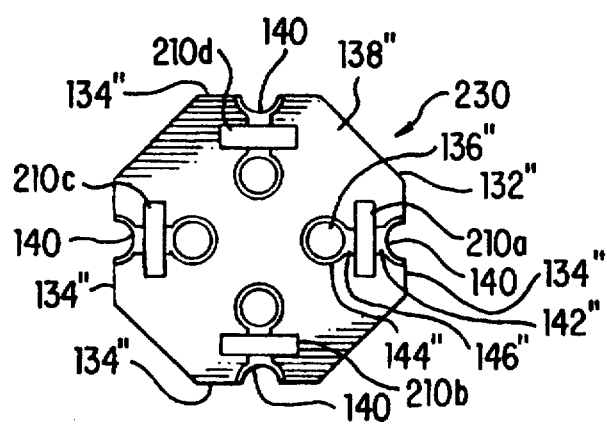
FIG. 12 is a top plan view of an alternate embodiment of the multi-lead capacitor support assembly of the present invention; and, FIG. 13 is an enlarged sectional view of a portion of the multi-lead capacitor support assembly of the present invention.

Referring now to FIG. 12, there is shown a capacitor support assembly 230 for use with multi-lead feedthroughs. Although the capacitor support assembly 230 is shown for coupling to a multi-lead feedthrough, the concepts embodied therein are equally applicable to the single lead filtered feedthrough 100, previously discussed. The capacitor support assembly 230 includes a polygonal-shaped insulative substrate 132" having an upper surface 138" and a plurality of metallized apertures 136" formed therethrough. Surrounding each of the apertures 136" there is provided a metallized annular region 144" with a metallized extended area 146" extending therefrom. An adjacent perimeter edge 134" is formed with a metallized edge recess 140 with a metallized upper edge region 142 being electrically coupled thereto. Between each of the regions 146" and 142" there is disposed a respective capacitive element 210a, 210b, 210c and 210d, respectively. As opposed to the capacitive elements being chip capacitors, the capacitive elements 210a–210b are film-type capacitors which are screened onto the substrate surface 138". Such capacitive elements may be formed by a thick or thin film technology which is applied to the substrate 132" so that the capacitors are formed in-place. The capacitor support assembly 230 is applied to the multi-lead feedthrough 10', shown in FIGS. 5B or 5C, in the manner previously discussed, utilizing an insulative material 122, 122' and the conductive contact materials 150 and 152. The embodiment shown in FIG. 12 is exemplary and the inventive concepts being disclosed are not restricted to the particular configuration shown in the FIG. The inventive concepts embodied herein include the use of discoidal type capacitors or other capacitor structures mounted on substrate 132, 132'.

Figure 11A:
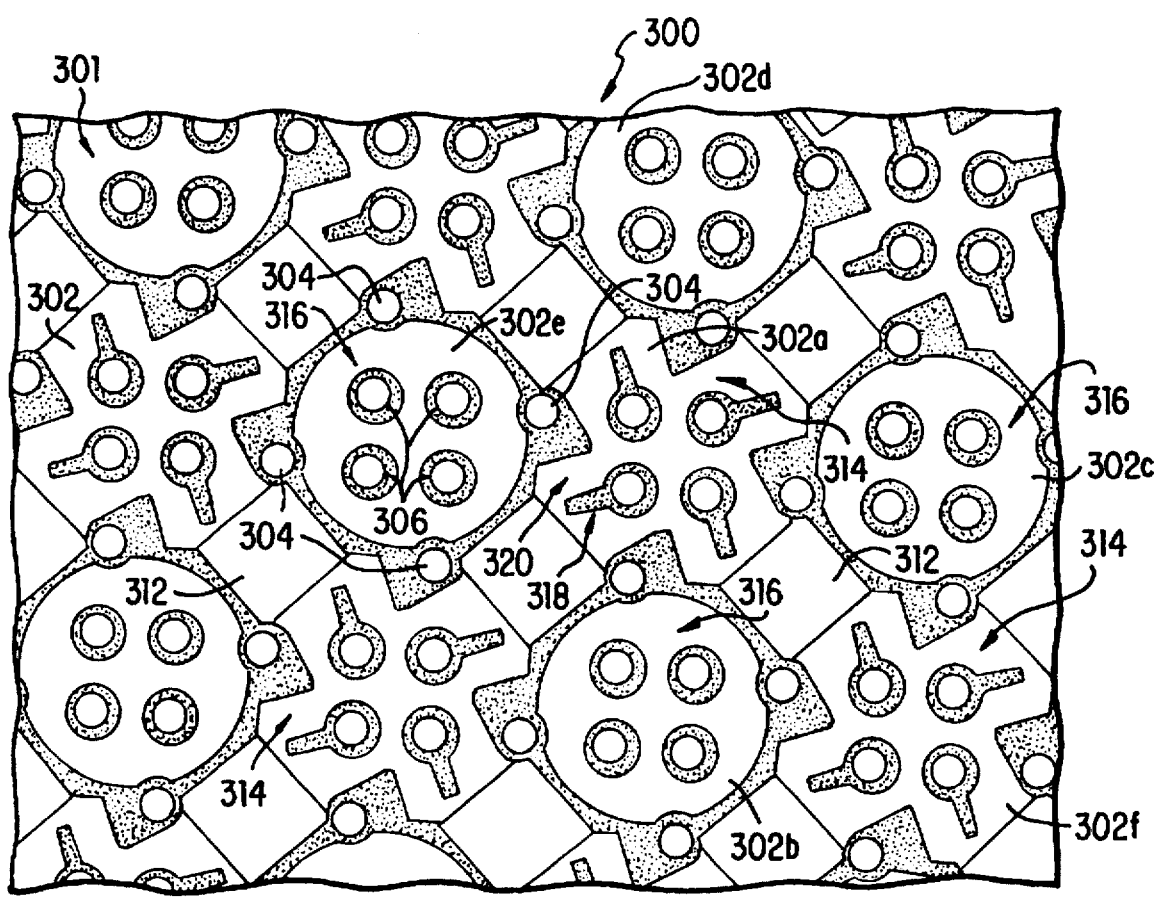
FIG. 11A is a plan view of a section of an array of substrate sections of the present invention.
Figure 11B:
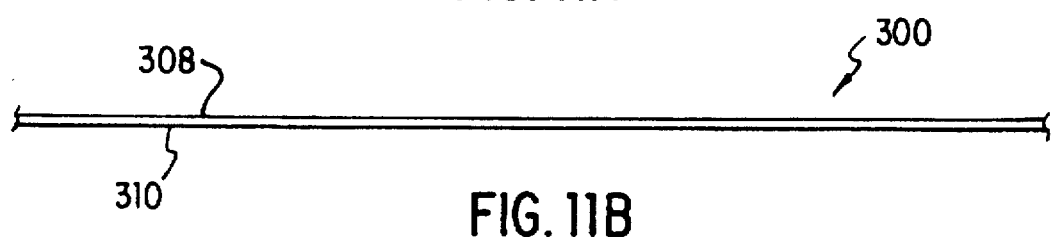
FIG. 11B is an elevation view of the insulative sheet material of the present invention.

An important aspect of the instant invention is the efficiency by which the substrate 130' may be manufactured. Referring to FIGS. 11A and 11B, there is shown, a sheet of insulative material 300 on which is formed an array 301 of substrate sections 302, each substrate section 302 defining an individual substrate 132' when separated from the sheet of material. As is customary, the upper surface 308 and lower surface 310 of the sheet of insulative material 300 carries a metallization layer which is patterned either preceding or after the desired openings are formed through the material. Lastly, the insulative material 300 is scored to define each of the substrate sections 302 and "snapped" to separate one substrate section from another. As shown, each of the metallized edge recesses 140' of substrate 132' is formed by a perimeter edge through opening 304 formed through the insulative sheet material 300. As discussed earlier, the capacitors which are mounted on each substrate 132' are offset such that the respective metallized edge recess 140' is located off-center on each associated edge 134', the metallized edge recesses being located adjacent a respective vertex of the polygonal perimeter edge. Thus, the polygonal contour of each of the substrate sections 302 permits formation of an array 301 of substrate sections, with one section being in abutting relationship with another on each of four sides thereof. However, the off-center location of the edge recess 140 would require fifty percent of the substrate sections to be discarded if all of the substrate sections carried the same metallization pattern thereon, as the recess section 140 would be improperly located on one-half the units. Alternately, each substrate section would have to be spaced one from another, wasting material and requiring more processing steps to produce the substrates. To overcome this problem, the array 301 is defined by a portion thereof having first metallization pattern 314 formed thereon, with such substrate sections being disposed adjacent other substrate sections having the second metallization pattern 320 formed thereon, in both the X and Y directions of the planar array. The opposing surface 310, likewise, is provided with substrate sections 302 having both the first and second metallization patterns formed thereon, disposed in opposing relationship with respect to the upper surface 308 arrangement of metallization patterns. Thus, when a particular substrate section 302a is formed with the first metallization pattern 314 formed on the upper surface 308 of insulative sheet 300, that substrate section 302a will have the second metallization pattern 316 formed on the lower surface 310 of the insulative sheet.

Conversely, the particular substrate section 302b is formed with the second metallization pattern 316 formed on the upper section 308 of the sheet material 300, the opposing bottom surface 310 being formed with the first metallization pattern thereon. As previously stated, by this arrangement, each of the adjacent substrate sections 302b, 302c, 302d and 302e has a metallization pattern which is opposite to that of substrate section 302a. Accordingly, when the substrate sections 302 are separated one from another, all of the respective edge recesses 140' will be properly located with respect to the metallization patterns required to properly locate capacitors on the substrates 132'. In addition to the perimeter edge through openings 304 which are formed through the sheet material 300, each substrate section 302 is processed to form a plurality of interior through openings 306 which will define the metallized apertures 136 of the substrate 132'.

Further, as each of the substrate sections 302 has a polygonal contour, the sheet material 300 will have quadrilateral areas defined between each grouping of four substrate sections of the array. Such quadrilateral areas are removed to form quadrilateral openings 312. Thus, between the adjacent substrate sections 302a, 302c, 302f and 302b, a quadrilateral opening 312 is formed prior to the separation of one substrate section from another. The formation of the quadrilateral openings 312, the perimeter edge through openings 304 and the interior through openings 306 may be formed by mechanical machining, laser cutting, chemical etching or other like means. Where insulative sheet 300 is formed by a material which is cast or moldable, the openings may be formed at the time of sheet formation. Subsequent to formation of the metallized patterns, the interface between adjacent substrate sections 302 is defined by a scoring operation which then permits each section 302 to be separated one from another, by techniques well known in the semiconductor and ceramic substrate arts.

The manufacture of substrates 132 and 132" are very similar to that just described for substrate 132'. As the metallized recesses 140 for each of the substrates 132 and 132" are centrally located on a respective edge 134, 134", there is no reason to utilize different metallization patterns on the same side of the substrate. Thus, in the manufacture of substrates 132 and 132" the upper surface 308 of the sheet of insulative material 300 would all carry the same metallization pattern, with the opposing side 310 thereof being formed with the other metallization pattern.

In summary, the filtered feedthrough 100, 200 is provided with a first metallization area formed by a metallized annular region 144, and a metallized extended area 146. By that arrangement, the capacitor can be electrically coupled to the feedthrough lead 12 through its electrical coupling with the pad formed by the extended area 146. By displacing the capacitor from the lead, a better access to the area surrounding the lead is achieved to better apply conductive contact material 152 within the metallized apertures 136 in the area surrounding the lead 12 and the metallized annular region 144 surrounding the metallized aperture 136. Such provides improved reliability for the filtered feedthrough assembly, insuring a solid bond between the metallization pattern and the lead, as well as insuring adequate coupling of the capacitor to the metallization pattern. Further, by angling the metallized extended area 146, large capacitors can be accommodated within the confines of the perimeter edge of the substrate. The capacitive elements used can be chip capacitors, film-type capacitors that are formed in-place, or discoidal type capacitors that are positioned coaxially with the feedthrough leads, but mounted on the substrate. The formation of metallized recesses 140, 140' in edge portions 134, 134' of the substrate provides a convenient location by which an electrical coupling can be made between the metallized upper edge region 142 and the ferrule of the feedthrough, the recessed area allows the conductive contact material 150 to be applied therein, while not extending outside the perimeter edge of the substrate. By that arrangement, adequate space remains for the encapsulation material, providing a sufficient insulation thickness to adequately protect the electrical connection, and prevent any migration of constituents (ions, toxins, etc.) from within the encapsulated region. The metallized recesses 140, 140' also provide a protected conduction path between the respective conductive patterns on the upper and lower sides of the substrate. As the edge metallization is disposed within recesses, it is much less likely to be damaged during the manufacturing process, thereby increasing the reliability of the filtered feedthrough device.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A filtered feedthrough assembly, comprising:

a conductive feedthrough including (a) a metallic ferrule having opposing first and second ends and a centrally disposed through opening extending between said first and second ends, (b) at least one elongate lead wire extending through said ferrule through opening, and (c) means for forming a hermetic seal between said lead wire and said ferrule disposed within said ferrule through opening;

filter support means disposed at an end surface of said conductive feedthrough, said filter support means including an insulative substrate having a polygonal perimeter edge and at least one aperture formed therein for passage of said lead wire therethrough, said substrate having (a) an upper surface with at least one first metallization area adjacent said at least one aperture and at least one second metallization area adjacent a perimeter portion thereof, and (b) an opposing lower surface;

at least one capacitor disposed on said filter support means electrically coupled between said first metallization area and said second metallization area;

means for electrically coupling said first metallization area to said lead wire; and, means for electrically coupling said second metallization area to said ferrule.

2. A filtered feedthrough assembly, comprising:

a conductive feedthrough including (a) a metallic ferrule having opposing first and second ends and a centrally disposed through opening extending between said first and second ends, (b) at least one elongate lead wire extending through said ferrule through opening, and (c) means for forming a hermetic seal between said lead wire and said ferrule disposed within said ferrule through opening;

filter support means disposed at an end surface of the hermetic seal means of said conductive feedthrough, said filter support means including an insulative substrate having at least one aperture formed therein for passage of said lead wire therethrough, said substrate having (a) an upper surface with at least one first metallization area adjacent said at least one aperture and at least one second metallization area adjacent a perimeter portion thereof, said first and second metallization areas each having a mounting pad extending therefrom, and (b) an opposing lower surface;

at least one capacitor coupled to said filter support means, said capacitor being electrically coupled between said mounting pads of said first metallization area and said second metallization area;

means for electrically coupling said first metallization area to said lead wire; and, means for electrically coupling said second metallization area to said ferrule.

3. The filtered feedthrough assembly as recited in claim 2 further comprising an insulative material layer disposed between said lower surface of said substrate and said end surface of the hermetic seal means of said conductive feedthrough.

4. The filtered feedthrough assembly as recited in claim 2 where said substrate has a perimeter edge having a plurality of angularly spaced recesses formed therein, said means for electrically coupling said second metallization area to said ferrule including a metallization of each of said recesses, and an electrical coupling between at least one of said recess metallizations and said second metallization area.

5. The filtered feedthrough assembly as recited in claim 4 where said substrate has a substantially annular metallization area disposed adjacent said perimeter edge and electrically coupled to each of said plurality of recess metallizations.

6. The filtered feedthrough assembly as recited in claim 5 where said means for electrically coupling said second metallization area to said ferrule includes means for joining each of said plurality of recesses to said ferrule.

7. The filtered feedthrough assembly as recited in claim 2 where said at least one capacitor is a chip capacitor having a parallelepiped contour, said chip capacitor having a pair of metallized contacts formed on opposing end portions thereof and electrically coupled to a respective one of said first and second metallization areas.

8. The filtered feedthrough assembly as recited in claim 2 where said at least one capacitor is a film-type capacitor formed on said substrate.

9. The filtered feedthrough assembly as recited in claim 4 where said substrate is one of a plurality of substrate sections formed as an array, said array being metallized prior to said substrate being separated therefrom.

10. A multi-lead filtered feedthrough assembly, comprising:

a conductive multi-lead feedthrough including (a) a metallic ferrule having opposing first and second ends and a centrally disposed through opening extending between said first and second ends, (b) a plurality of elongate lead wires extending through said ferrule through opening, and (c) means for forming a hermetic seal between said plurality of lead wires and said ferrule disposed within said ferrule through opening;

filter support means disposed at an end surface of said conductive multi-lead feedthrough, said filter support means including an insulative substrate having a plurality of apertures formed therein for respective passage of said plurality of lead wires therethrough, said substrate having (a) an upper surface with a first metallization pattern defined by plurality of first metallization areas respectively disposed adjacent said plurality of apertures and a plurality of second metallization areas disposed adjacent a respective perimeter portion thereof, and (b) an opposing lower surface with a second metallization pattern;

a plurality of capacitors, each of said plurality of capacitors being disposed on said filter support means and coupled between a respective one of said plurality of first metallization areas and a respective one of said plurality of second metallization areas; and, means for electrically coupling each of said first metallization areas to a respective one of said lead wires and each of said second metallization areas to said ferrule.

11. The multi-lead filtered feedthrough assembly as recited in claim 10 where each of said plurality of capacitors is a chip capacitor having a parallelepiped contour, each of said chip capacitors having a pair of metallized contacts formed on opposing end portions of said chip capacitor.

12. The multi-lead filtered feedthrough assembly as recited in claim 10 where said substrate has a perimeter edge having a plurality of angularly spaced recesses formed therein, each of said recesses being metallized and electrically coupled to said second metallization area.

13. The filtered feedthrough assembly as recited in claim 12 where said substrate includes a substantially annular metallization area disposed adjacent said perimeter edge and electrically coupled to each of said plurality of metallized recesses.

14. The filtered feedthrough assembly as recited in claim 12 where said means for electrically coupling includes means for joining each of said plurality of recesses to said ferrule.

15. The filtered feedthrough assembly as recited in claim 12 where said perimeter edge has a polygonal contour and each of said plurality of metallized recesses is located adjacent a respective vertex of said polygonal perimeter edge.

16. The multi-lead filtered feedthrough assembly as recited in claim 10 further comprising an insulative material layer disposed between said lower surface of said substrate and said end surface of said conductive feedthrough.

17. The multi-lead filtered feedthrough assembly as recited in claim 10 where said substrate is one of a plurality of substrate sections formed as an array, said array having opposing first and second surfaces metallized prior to said substrate being separated therefrom.

18. The multi-lead filtered feedthrough assembly as recited in claim 17 where said first metallized surface of said array is defined by a respective one of said plurality of substrate sections having said first metallization pattern formed thereon being disposed adjacent others of said plurality of substrate sections having said second metallization pattern formed thereon and one of said plurality of substrate sections having said second metallization pattern formed thereon being disposed adjacent others of said plurality of substrate sections having said first metallization pattern formed thereon.

19. The multi-lead filtered feedthrough assembly as recited in claim 18 where said second metallized surface of said array is defined by said respective substrate sections having said second metallization pattern formed thereon and being disposed adjacent others of said plurality of substrate sections having said first metallization pattern formed thereon and one of said plurality of substrate sections having said first metallization pattern formed thereon being disposed adjacent others of said plurality of substrate sections having said second metallization pattern formed thereon.

20. The multi-lead filtered feedthrough assembly as recited in claim 12 where each of said capacitors are oriented angularly within an approximately range of 15°–45° with respect to an adjacent side of said perimeter edge.

21. The multi-lead filtered feedthrough assembly as recited in claim 10 where each of said plurality of capacitors is a film type capacitor formed in-place on said substrate.

22. A method of adding a capacitor filter to a feedthrough assembly, comprising the steps of:

a. forming an array of substrate sections on a sheet of insulative material, each of said substrate sections having a polygonal perimeter edge and at least one aperture formed between opposing surfaces of said substrate section within said polygonal perimeter edge, one of said opposing surfaces of each of said substrate sections having a first metallization pattern formed thereon, said first metallization pattern being defined by at least one first metallization area disposed adjacent said at least one aperture and at least one second metallization area disposed adjacent said polygonal perimeter edge;

b. separating said array of substrate sections into a plurality of polygonal shaped substrates;

c. providing a capacitive element on one of said plurality of substrates, said capacitive element being electrically coupled between said first and second metallization areas;

d. providing a feedthrough assembly having a ferrule, at least one lead wire extending through an opening formed in said ferrule, and means for hermetically sealing said lead wire and said ferrule;

e. positioning said substrate on an end surface of said feedthrough with said lead wire passing through said aperture; and, f. electrically coupling said first and second metallization areas respectively to said lead wire and said ferrule.

23. The method as recited in claim 22 where said step of forming an array of substrate sections includes the step of forming a plurality of metallized recesses in said polygonal perimeter edge.

24. The method as recited in claim 22 where said step of electrically coupling includes the step electrically joining said plurality of metallized recesses with said ferrule.

25. The method as recited in claim 22 where said step of positioning said substrate on an end surface of said feedthrough is preceded by the step of applying a bead of non-conductive polymer to said end surface of said feedthrough.

26. The method as recited in claim 22 where said step of positioning said substrate on an end surface of said feedthrough is preceded by the step of positioning a sheet of insulating material between said end surface of said feedthrough and said substrate.

27. The method as recited in claim 22 where said step of forming an array of substrate sections includes the step of forming a second metallization pattern on said other opposing surface of each said substrate sections.

28. The method as recited in claim 27 where said step of forming an array of substrate sections further includes the step of forming a respective one of said plurality of substrate sections with said first metallization pattern formed thereon being disposed adjacent others of said plurality of substrate sections having said second metallization pattern formed thereon and one of said plurality of substrate sections having said second metallization pattern formed thereon being disposed adjacent others of said plurality of substrate sections having said first metallization pattern formed thereon.

29. The method as recited in claim 23 where said step of forming a plurality of metallized recesses in said polygonal perimeter edge is preceded by the step of forming a plurality of apertures through said sheet of insulative material, each of said plurality of apertures encompassing a respective polygonal perimeter edge portion of a respective two adjoining substrate sections.

30. A filtered feedthrough assembly, comprising:

a conductive feedthrough including (a) a metallic ferrule having opposing first and second ends and a centrally disposed through opening extending between said first and second ends, (b) at least one elongate lead wire extending through said ferrule through opening, and (c) means for forming a hermetic seal between said lead wire and said ferrule disposed within said ferrule through opening;

at least one chip capacitor having a pair of connection terminals, said chip capacitor having one of said pair of connection terminals electrically coupled to said ferrule; and, an insulative substrate disposed on an end surface of said conductive feedthrough and having at least one aperture formed therein for passage of said lead wire therethrough, said substrate having at least one surface with at least one metallization pattern formed thereon, said metallization pattern including a mounting pad for connection with the other of said pair of connection terminals of said capacitor to provide an electrical connection between capacitor and said lead wire.

* * * * *